Figure 1:
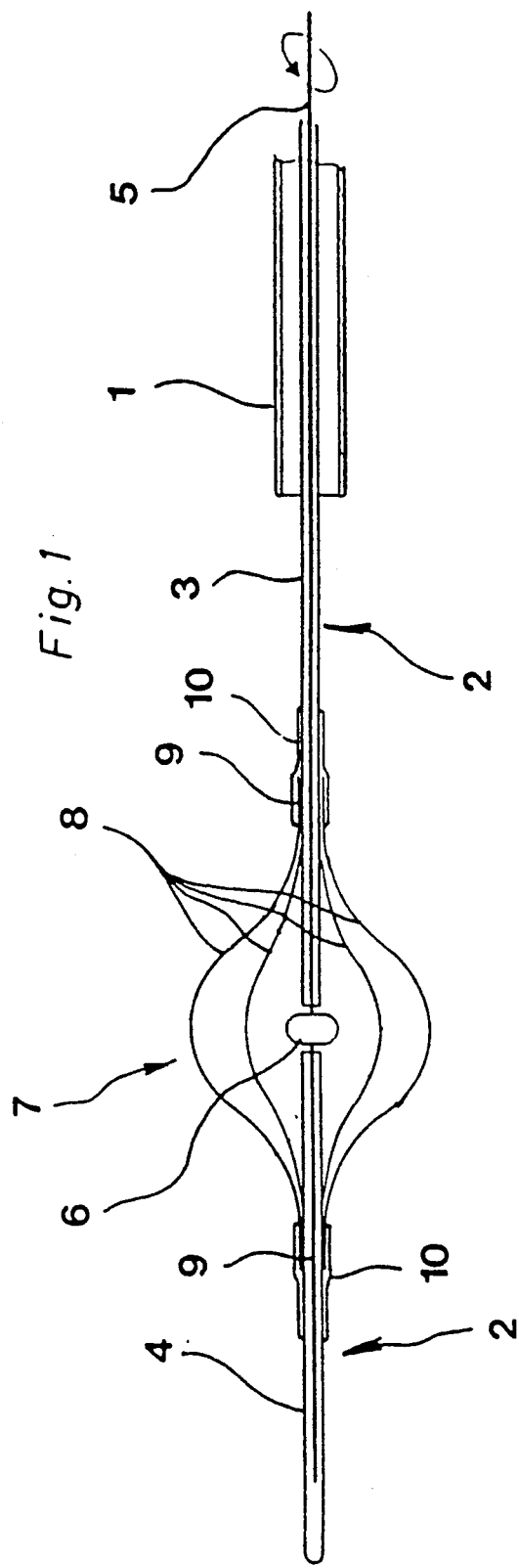

United States Patent
Günther et al.

[11] Patent Number: 5,330,484
[45] Date of Patent: Jul. 19, 1994

[54] DEVICE FOR FRAGMENTATION OF THROMBI

[75] Inventors: Rolf W. Günther; Thomas Schmitz-Rode, both of Aachen, Fed. Rep. of Germany

[73] Assignee: William Cook Europe A/S, Denmark

[21] Appl. No.: 969,296

[22] PCT Filed: Aug. 13, 1991

[86] PCT No.: PCT/DK91/00227
§ 371 Date: Feb. 16, 1993
§ 102(e) Date: Feb. 16, 1993

[87] PCT Pub. No.: WO92/03098
PCT Pub. Date: Mar. 5, 1992

[30] Foreign Application Priority Data

Aug. 16, 1990 [DE] Fed. Rep. of Germany ....... 4025825

[51] Int. Cl.⁵ .............................................. A61B 17/22
[52] U.S. Cl. ................................... 606/128; 606/127; 606/113

[58] Field of Search ................... 606/1, 127, 128, 113, 606/114, 190, 194; 604/164, 264, 272; 128/657, 772

[56] References Cited

U.S. PATENT DOCUMENTS 4,811,735  3/1989  Nash et al. .

FOREIGN PATENT DOCUMENTS 0117519  9/1984  European Pat. Off. .
0337918  10/1989  European Pat. Off. .
0367982  5/1990  European Pat. Off. .
8802243  4/1988  World Int. Prop. O. .

Primary Examiner—Stephen C. Pellegrino
Assistant Examiner—Glenn Dawson
Attorney, Agent, or Firm—Richard J. Godlewski

[57] ABSTRACT

Thrombi are fragmented by a rotating action body secured on a torsion-resistant flexible shaft. The shaft is journalled in two parts of an internal catheter between which the action body is located. A grid surrounding the action body is formed by curved biased resilient legs which connect the two parts of the internal catheter together.

8 Claims, 1 Drawing Sheet

DEVICE FOR FRAGMENTATION OF THROMBI

The invention relates to a device for fragmentation of thrombi, comprising an external catheter, an internal catheter passed through the external catheter, a torsion-resistant flexible shaft journalled in the internal catheter, a fast rotating drive means for said shaft at the proximal end of the external catheter and an action body connected with the shaft to be unturnable thereto.

Such devices are known in various designs and serve for percutaneous recanalization of blood vessels. An action body arranged at the distal end of the catheter of devices, e.g. in the form of a twin-bladed propeller driven by a shaft journalled in the interior of the catheter serve to fragment thrombi in the blood vessel thereby to restore a free flow passage for the blood through the vessel.

According to their mode of operation the prior devices may be divided into two groups:

In devices of a first group, such as from EP-Al-0367982, fragmentation of the thrombi is performed by means of a propeller-like action body with cutting blades in the area of the catheter tip, accompanied by simultaneous transcatheteral evacuation of the thrombi fragments.

A significant disadvantages of such devices operating with transcatheteral aspiration results from the tendency of the catheter tip to be displaced by insufficiently fragmented thrombi, whereby a further determined processing of the thrombi will be prevented. In particular, this disadvantage has a serious effect in case of fibrin-containing and/or large quantities of thrombi.

In devices of a second group, such as known from U.S. Pat. No. 4,747,821 the fragmentation of thrombi is performed by means of an action body arranged in the area of the catheter tip and being caused to rotate at up to 100,000 r.p.m. The high rotational speed of the action body causes thrombi to be sucked into the action volume and results in a through fragmentation of the thrombi.

A significant disadvantage of these devices operating without transcatheteral aspiration follows from the risk of damage to the walls of the vessel by the action body in spite of a to a large extent curved external shape of the latter.

To counteract the risk of damaging the walls of the vessel, a device has been suggested in the published international patent application WO-A-88/00243 in which a rigid metallic envelope having an opening at one end as well as several radial openings distributed over the circumference surrounds the action body. Even if the rigid metallic envelope eliminates the risk of direct contact and thereby damage to the walls of the vessel by the action body it is a disadvantage that the openings of the envelope easily get blocked by thrombi, in particular as a result of the fibrin fibres contained therein. Moreover, the operation of this device is affected by the fact that the narrow annular clearance between the inner side of the rigid envelope and the outer side of the action body will be further narrowed by fibrin fibres winding around the action body. In addition, the narrow enclosure of the action body influences the transfer of the high rotational velocity to the surrounding liquid. Thereby, the vortex formation and suction effect resulting therefrom will be very limited.

It is an object of the invention to provide a device of the above-mentioned kind of such a design that while maintaining the operation in respect of fragmentation of thrombi into small particles by means of a fast rotating action body, the risk of damages to the vessel is eliminated without any need to enclose the action body in a rigid, protective envelope which affects the suction action on the thrombus.

To accomplish this, a fragmentation device according to the invention is characterized in that the internal catheter is composed of a proximal and a distal part, between which the action body is arranged with the shaft of the action body journalled in both parts of the internal catheter, the action body being concentrically surrounded by a resiliently deformable grid body, comprising legs through which the two parts of the internal catheter are connected with each other. By the division of internal catheter in a relatively long proximal catheter part and a relatively short distal catheter part, the action body may be arranged between the two parts close to the catheter tip.

From U.S. Pat. No. 4,811,735 an apparatus for disintegrating a stone, such as a gallstone, is known, comprising a high-speed rotating working head which in use is positioned adjacent to the stone. The working head is surrounded by a shroud guide, comprising a plurality of equidistantly spaced prongs and serving to protect the wall of the gall bladder from the rotating blades of the working head and to direct stones towards the working head.

By journalling the shaft in both catheter parts, the action body extending radially beyond the circumference of the internal catheter, is not floating as in the prior art devices, but journalled on both sides and thereby significantly stabilized. By means of the resiliently deformable grid body the wall of the vessel will be kept away from the action body, while the latter is rotating in the centre of the vessel cross section, and thrombi will be sucked on essentially without hindrances through the large clearances between the grid legs as a result of the hydrodynamic effect. Moreover, the grid legs entail a safe connection of the two catheter parts which according to the actual degree of deformation of the grid legs may assume a varying axial separation from one another, reaching its maximum by fully stretched grid legs while maintaining the distal end part of the shaft safely journalled in the distal part of the internal catheter also in this condition.

In a particularly advantageous embodiment of the invention the grid body consists exclusively of resilient legs extending in the longitudinal direction of the catheter and being radially outwardly biassed into a semicircular shape such that the grid body in a radially compressed and axially extended condition may be passed through the aperture of the external catheter and automatically expand into a balloon-shape outside the external catheter.

By this design the internal catheter with the action body journalled between its two parts may be passed through the external catheter, whereby the grid legs are held in stretched form close to the action body and may slide along the internal wall of the external catheter at the outlet of which the grid legs are again spread automatically into their curved form as a result of their bias until they come into contact with the wall of the vessel.

In a further embodiment of the invention the ends of the resilient legs are inserted in a socket arranged on one part of the internal catheter and retained between the external side of the internal catheter and the internal side of the socket.

By this measure a stable connection of the two parts of the internal catheter is safeguarded on the one hand and, on the other hand, it is excluded that the ends of the grid legs may give rise to any risk of damaging the wall of the vessel.

To avoid damage to the wall of the vessel by the distal end of the internal catheter, an embodiment of the invention may finally be characterized in that this end is closed and formed into a hemispherical shape.

In the following, an embodiment of the device according to the invention will be further explained with reference to the drawings, in which FIG. 1 is a longitudinal sectional view, in part, of the device in its working position.

An internal catheter 2 is passed through an external catheter 1 and consists of a relatively long part 3 and a very short part 4. In both parts 3, 4 is arranged a continuous torsion-resistant shaft 5, which by drive means arranged outside the proximal end of the external catheter 1 may be rotated at a high velocity.

Between the two parts 3, 4 an action body 6 is arranged on the shaft 5 to be non-turnable relative thereto, which action body is defined both in the axial and radial directions by an oval or elliptical contour. However, the action body 6 may also have an axial cross section substantially in the form of a parallelogram having an acute cutting edge at two diametrically opposite sides, whereas pairs of flanks of the cutting edges designed in this way join each other under obtuse angles. In general, the design of the action body 6 may be directed to the sole purpose to cause a hydrodynamic suction effect and a mechanical fragmentation effect, whereby damages to the walls of the vessel are excluded, even by a very sharp-edged design of the action body 6, by means of a balloon-shaped grid body 7 arranged around the rotating action body 6.

The grid body 7 consists of six curved biased legs 8 of spring wire, the ends of which are adhesively secured or soldered in sockets 10 which are pushed onto and secured on the parts 3 and 4 of the internal catheter 2.

The distal end of the part 4 is closed and rounded into a convex hemispherical form so that the tip of the internal catheter 2 after having left the distal end of the external catheter 1 will not damage the wall of the vessel on its further passage through the vessel. The hemispherical form of the flexible catheter tip makes it furthermore possible to push this tip past a thrombus by means of the external catheter which initially surrounds the action body 6 and the legs 8 engaging it in a stretched condition.

When the device is positioned in this way for recanalization of a vessel, the external catheter 1 may be retracted over the internal catheter 2, so that the stretched legs 8 as a result of their bias assume a curved form on the outflow side of the thrombus and are spread to contact the wall of the vessel, whereby the grid body 7 thus formed assumes a balloon-shape concentrically surrounding the action body 6.

By a disadvantageous location the thrombus may be displaced by means of the balloon-shaped grid body 7 by retracting the entire device a corresponding distance out of the blood vessel.

When the suction and fragmentation of the thrombus has been accomplished at high rotational velocity of the action body 6, the internal catheter 2 with the action body 6 and the legs 8 is drawn into the external catheter 1 and removed together therewith.

We claim:

1. A device for fragmentation of thrombi, comprising an external catheter having, an inner lumen/an internal catheter passed through the external catheter, a torsion-resistant flexible shaft journalled in the internal catheter, and an action body connected with the flexible shaft to be fixed relative to the flexible shaft, characterized in that the internal catheter (2) is composed of a proximal and a distal part (3, 4), between which the action body (6) is arranged with the flexible shaft being (5) (6) journalled in both parts (3,4) of the internal catheter, the action body (6) being concentrically surrounded by a resiliently deformable grid body (7), comprising legs (8) by which the distal and proximal parts (3, 4) of the internal catheter are connected with each other.

2. A device as claimed in claim 1, characterized in that the legs of the grid body (7) are resilient and external extending in a longitudinal direction of the internal catheter and are radially outwardly biassed into a semiconductor shape such that the grid body (7) in a radially compressed and axially extended condition may be passed through the inner lumen of the external catheter and automatically expand into a balloon-shape outside the external catheter (1).

3. A device as claimed in claim 2 characterized in that each end of the legs (8) is inserted in a socket (10) arranged on at least one of the distal and proximal parts (3, 4) of the internal catheter (2) and retained between an external side of the internal catheter (2) and an internal side of the socket (10).

4. A device as claim 3 characterized in that the internal catheter is closed and shaped into a hemispherical form at a distal end thereof.

5. A device as claimed in claim 2 characterized in that the internal catheter is closed and shaped into a hemispherical form at a distal end thereof.

6. A device as claimed in claim 1 characterized in that each end of the legs (8) is inserted in a socket (10) arranged on at least one of the distal and proximal parts (3, 4) of the internal catheter (2) and retained between an external side of the internal catheter (2) and an internal side of the socket (10).

7. A device as claimed in claim 6 characterized in that the internal catheter is closed and shaped into a hemispherical form at a distal end thereof.

8. A device as claimed in claim 1 characterized in that the internal catheter is closed and shaped into a hemispherical form at a distal end thereof.

* * * * *